(12) United States Patent
Takase et al.

(10) Patent No.: US 10,018,605 B2
(45) Date of Patent: Jul. 10, 2018

(54) METHOD FOR MEASURING DISSOLVED OXYGEN OF OXYGEN WATER

(71) Applicants: MediScience Espoir Inc., Kanagawa (JP); Sanyo Kako Co., Ltd., Tokyo (JP)

(72) Inventors: Azuma Takase, Tokyo (JP); Akira Sumiyoshi, Tokyo (JP); Takaaki Matsumoto, Kanagawa (JP); Toshikatsu Hagiwara, Kanagawa (JP)

(73) Assignees: MEDISCIENCE ESPOIR INC., Kanagawa (JP); SANYO KAKO CO., LTD., Tokyo (JP)

(*) Notice: Subject to any disclaimer, the term of this patent is extended or adjusted under 35 U.S.C. 154(b) by 0 days.

(21) Appl. No.: 15/502,603

(22) PCT Filed: Aug. 10, 2015

(86) PCT No.: PCT/JP2015/072701
§ 371 (c)(1),
(2) Date: Feb. 8, 2017

(87) PCT Pub. No.: WO2016/024574
PCT Pub. Date: Feb. 18, 2016

(65) Prior Publication Data
US 2017/0248563 A1 Aug. 31, 2017

(30) Foreign Application Priority Data
Aug. 11, 2014 (JP) .................. 2014-163715

(51) Int. Cl.
| | | |
|---|---|---|
| *G01N 31/16* | (2006.01) | |
| *G01N 31/00* | (2006.01) | |
| *G01N 21/77* | (2006.01) | |
| *G01N 21/79* | (2006.01) | |
| *G01N 31/22* | (2006.01) | |

(52) U.S. Cl.
CPC ............. *G01N 31/16* (2013.01); *G01N 31/00* (2013.01); *G01N 31/225* (2013.01); *G01N 21/77* (2013.01); *G01N 21/79* (2013.01); *Y10T 436/209163* (2015.01)

(58) Field of Classification Search
CPC ...... G01N 31/16; G01N 31/225; G01N 31/00; G01N 21/77; G01N 21/79; Y10T 436/17; Y10T 436/173845; Y10T 436/19; Y10T 436/193333; Y10T 436/20; Y10T 436/203332; Y10T 436/209163
USPC ....... 436/106, 111, 124, 125, 127, 131, 136, 436/138, 147, 163; 422/75
See application file for complete search history.

(56) References Cited

U.S. PATENT DOCUMENTS

| | | | |
|---|---|---|---|
| 4,269,717 A * | 5/1981 | Slovinsky ................. | C02F 1/20 210/750 |
| 5,415,809 A * | 5/1995 | Elson ..................... | G01N 21/78 116/206 |
| 6,391,256 B1 * | 5/2002 | Moon ....................... | C02F 1/20 210/750 |
| 2015/0159072 A1 * | 6/2015 | Hale ........................ | C09K 8/06 507/132 |

* cited by examiner

*Primary Examiner* — Maureen Wallenhorst
(74) *Attorney, Agent, or Firm* — Wenderoth, Lind & Ponack, L.L.P.

(57) ABSTRACT

A method for measuring an amount of dissolved oxygen contained in a liquid sample, including the steps of: (1) adding a deoxygenating amino compound to a liquid sample to prepare the liquid sample having a predetermined concentration of the deoxygenating amino compound; (2) after Step (1), heating the liquid sample containing the deoxygenating amino compound at a temperature of 80° C. or more; (3) after Step (2), measuring the concentration of the deoxygenating amino compound contained in the liquid sample; and (4) calculating the amount of the dissolved oxygen contained in the liquid sample in Step (1) from the amount of the reacted deoxygenating amino compound by comparing the concentration of the deoxygenating amino compound measured in Step (3) and the concentration of the deoxygenating amino compound measured in Step (1).

4 Claims, No Drawings

METHOD FOR MEASURING DISSOLVED OXYGEN OF OXYGEN WATER

TECHNICAL FIELD

The present invention relates to a method for measuring an amount of dissolved oxygen, which enables the measurement of an amount of dissolved oxygen in oxygen water containing dissolved oxygen that has not been able to be measured by conventional measuring methods.

BACKGROUND ART

In Patent Literature 1, the applicant of the present application suggested a gas-liquid mixing apparatus that is configured to mix, dissolve and segmentalize substances of a liquid phase, a gas phase and a solid phase for fluids such as water. According to this gas-liquid mixing apparatus, for example, in the case when water and oxygen are used as materials, oxygen water (water in which oxygen is dissolved) having a characteristic that a state under which an amount of dissolved oxygen of 25 ppm or more is maintained for 35 days or more even under an open atmosphere can be produced. Furthermore, for the amount of the dissolved oxygen in such oxygen water, for example, various devices for measuring dissolved oxygen utilizing known methods such as a diaphragm electrode method, a Winkler method and a fluorescence method are used.

CITATION LIST

Patent Literature

Patent Literature 1: WO 2012/081682
Patent Literature 2: JP 2002-371389 A

SUMMARY OF INVENTION

Technical Problem

On the other hand, the applicant of the present application found that the oxygen water produced by the gas-liquid mixing apparatus of Patent Literature 1 has significant effects such as that a value of $SpO_2$ increases, by being drunk. Furthermore, the applicant confirmed that any increase in the value of $SpO_2$ by drinking is not observed in conventional commercially available oxygen waters even the amount of dissolved oxygen measured by an existing measuring method is similar to that of the oxygen water produced by the gas-liquid mixing apparatus of Patent Literature 1.

Furthermore, the applicant considered the cause of such phenomenon and reached a presumption that the oxygen water produced by the gas-liquid mixing apparatus of Patent Literature 1 would contain dissolved oxygen that cannot be measured by an existing measuring method in a state of a clathrate hydrate formed by oxygen molecules and water molecules, and then established a novel method for measuring an amount of dissolved oxygen.

The present invention was made in view of the above-mentioned circumstance, and aims at providing a method for measuring an amount of dissolved oxygen which enables measurement of an amount of dissolved oxygen in oxygen water containing dissolved oxygen that has not been able to be measured by conventional measuring methods.

Solution to Problem

To solve the above-mentioned problem, a method for measuring an amount of dissolved oxygen of the present invention is a method for measuring an amount of dissolved oxygen contained in a liquid sample, including the steps of:

(1) adding a deoxygenating amino compound to a liquid sample to prepare the liquid sample having a predetermined concentration of the deoxygenating amino compound;

(2) after Step (1), heating the liquid sample containing the deoxygenating amino compound at a temperature of 80° C. or more;

(3) after Step (2), measuring the concentration of the deoxygenating amino compound contained in the liquid sample; and (4) calculating the amount of the dissolved oxygen contained in the liquid sample in Step (1) from the amount of the reacted deoxygenating amino compound by comparing the concentration of the deoxygenating amino compound measured in Step (3) and the concentration of the deoxygenating amino compound measured in Step (1).

In this method for measuring an amount of dissolved oxygen, the deoxygenating amino compound is preferably one kind or two or more kinds from carbohydrazide, diethylhydroxylamine, hydroxydiaminobenzene and isopropylhydroxylamine.

In this method for measuring an amount of dissolved oxygen, the concentration of the deoxygenating amino compound in the liquid sample is preferably adjusted to 0.01 to 2% in Step (1).

In this method for measuring an amount of dissolved oxygen, the concentration of the deoxygenating amino compound in Step (3) is preferably measured by iodometry.

Advantageous Effects of Invention

According to the method for measuring an amount of dissolved oxygen of the present invention, an amount of dissolved oxygen in oxygen water containing dissolved oxygen that has not been able to be measured by conventional measuring methods can be properly measured.

DESCRIPTION OF EMBODIMENTS

The method for measuring an amount of dissolved oxygen of the present invention is a method for measuring an amount of dissolved oxygen in a liquid sample including the steps of:

(1) adding a deoxygenating amino compound to a liquid sample to prepare the liquid sample having a predetermined concentration of the deoxygenating amino compound;

(2) after Step (1), heating the liquid sample containing the deoxygenating amino compound at a temperature of 80° C. or more;

(3) after Step (2), measuring the concentration of the deoxygenating amino compound contained in the liquid sample; and (4) calculating the amount of the dissolved oxygen contained in the liquid sample in Step (1) from the amount of the reacted deoxygenating amino compound by comparing the concentration of the deoxygenating amino compound measured in Step (3) and the concentration of the deoxygenating amino compound measured in Step (1).

The respective steps will be explained below.

In Step (1), a deoxygenating amino compound is added to a liquid sample to prepare so as to a predetermined concentration.

The liquid sample is a liquid whose concentration of dissolved oxygen is to be measured, and oxygen waters (waters in which oxygen is dissolved) produced by various methods are generally exemplified. For example, in the case when commercially available oxygen water is selected as the liquid sample, the concentration of dissolved oxygen in the commercially available oxygen water can be properly measured.

As the deoxygenating amino compound, for example, one kind or two or more kinds from carbohydrazide, diethylhydroxylamine, hydroxydiaminobenzene and isopropylhydroxylamine can be exemplified, and among these, carbohydrazide is specifically preferable. For example, as described in Patent Literature 2 and the like, carbohydrazide has been conventionally used as an agent for removing oxygen in plants, boilers and the like. In plants, boilers and the like, when a trace amount of oxygen is contained in water to be supplied and the like, the oxygen causes corrosion of devices made of metal, and the like, and thus chemical removal of oxygen by a deoxygenating amino compound such as carbohydrazide is desired. The present invention focused on the reactivity of this deoxygenating amino compound with oxygen, and newly invented utilizing the deoxygenating amino compound for measuring an amount of dissolved oxygen.

Specifically, for example, in the case of carbohydrazide, it is known that the reaction of the following chemical formula 1 occurs under a condition of approximately 135° C. or less.

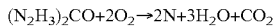

$$(N_2H_3)_2CO + 2O_2 \rightarrow 2N + 3H_2O + CO_2$$

The amount of the deoxygenating amino compound added to the liquid sample is not specifically limited, and for example, preparation can be conducted so that the concentration of the deoxygenating amino compound in the liquid sample becomes 0.01 to 2%. By adding the deoxygenating amino compound to be within this concentration range, the deoxygenating amino compound can be surely reacted with the oxygen contained in the liquid sample.

After Step (1), in Step (2), the liquid sample containing the deoxygenating amino compound is heated at a temperature of 80° C. or more.

The temperature for heating the liquid sample containing the deoxygenating amino compound is 80° C. or more, and is more preferably in the range of 80° C. to 120° C. The heating time depends on the amount of the liquid sample and the temperature, and for example, a tentative rough standard of the heating time can be about 3 to 4 hours in the case when the liquid sample is heated to 80° C., or about 30 minutes to 2 hours in the case when the liquid sample is heated to 100° C.

In the case when the deoxygenating amino compound is carbohydrazide, as shown in the above-mentioned chemical formula 1, the oxygen and carbohydrazide in the liquid sample are reacted by this step (2).

After Step (2), in Step (3), the concentration of the deoxygenating amino compound contained in the liquid sample is measured.

The method for measuring the concentration of the deoxygenating amino compound is not specifically limited, and for example, a known method such as iodometry (a redox titration method) can be suitably adopted.

In Step (4), the concentration of the deoxygenating amino compound measured in Step (3) and the concentration of the deoxygenating amino compound in Step (1) are compared, and the amount of the dissolved oxygen contained in the liquid sample of Step (1) is calculated from the amount of the reacted deoxygenating amino compound.

As in the carbohydrazide shown by the above-mentioned chemical formula 1, since the deoxygenating amino compound reacts with the oxygen in the liquid sample under a predetermined temperature condition, the amount of the dissolved oxygen contained in the liquid sample can be calculated from the concentrations of the deoxygenating amino compound before and after the reaction with consideration for the reaction formula.

In the method for measuring an amount of dissolved oxygen of the present invention, by heating the liquid sample, the whole oxygen contained in the liquid sample can be taken out and reacted with the deoxygenating amino compound (step (2)). Therefore, for example, the amount of dissolved oxygen in oxygen water (a liquid sample) containing dissolved oxygen that has not been able to be measured by conventional measuring methods can be properly measured.

Furthermore, for example, in the case when water and oxygen are mixed by utilizing the gas-liquid mixing system of Patent Literature 1, oxygen water having a characteristic that a state under which a concentration of dissolved oxygen of 25 ppm or more is maintained for 35 days or more under an open atmosphere can be produced.

It is considered from the researches that have been done until now that oxygen water produced by, for example, the method as mentioned above, is such that oxygen molecules are stably dissolved in the form of a clathrate hydrate surrounded by a lattice of water molecules. Therefore, it is considered that the whole oxygen that is dissolved in oxygen water in the state of a clathrate hydrate cannot be measured and thus the amount of the dissolved oxygen that is originally contained in oxygen water cannot be measured by a conventional method a diaphragm electrode method, a Winkler method or a fluorescence method.

On the other hand, the method for measuring dissolved oxygen of the present invention is such that the liquid sample (oxygen water) is reacted with the deoxygenating amino compound under heating (Step (2)). Therefore, the oxygen dissolved in the form of a clathrate hydrate in the liquid sample (oxygen water) is taken out, and thus the amount of dissolved oxygen that has not been able to be measured by conventional measuring methods can be properly measured.

Therefore, for example, in the case when there is a difference such that a numerical value P1 of the concentration of the dissolved oxygen in the liquid sample (oxygen water) which is measured by the method for measuring dissolved oxygen of the present invention and a numerical value P2 of a concentration of dissolved oxygen which is measured by a conventional method such as a diaphragm electrode method, a Winkler method or a fluorescence method is P1>P2, it is considered that the measured liquid sample contains oxygen that has not been able to be measured by conventional measuring methods, i.e., a clathrate hydrate containing oxygen molecules surrounded by a lattice of water molecules, which is dissolved in the liquid sample. Furthermore, oxygen water containing such clathrate hydrate exerts special effects that are not exerted by conventional oxygen waters, such as increase in a value of $SpO_2$, and thus can improve depression, COPD, decrease in pulmonary function, decrease in renal function and the like. Furthermore, the oxygen water can control skin conditions by being applied or sprayed onto skin, and thus can also be utilized as a cosmetic product. In addition, by providing the oxygen water of the present invention to a plant, the growth of the plant can be promoted.

Furthermore, for example, when seafood is maintained by the oxygen water of the present invention or ice obtained by freezing the oxygen water, the freshness of the seafood can be kept. Moreover, the oxygen water of the present invention also exerts effects such as maintenance of endurance during operation and restoration of strength, upon being drank.

The method for measuring dissolved oxygen of the present invention is not limited to the above-mentioned embodiments.

EXAMPLES

The embodiments of the method for measuring dissolved oxygen of the present invention will be explained below in detail together with Examples, but the method for measuring dissolved oxygen of the present invention is not limited to the following Examples at all.

<Example 1> Production of Oxygen Water

Oxygen water was produced by mixing oxygen and water by utilizing the gas-liquid mixing apparatus described in Patent Literature 1.

<Example 2> Measurement of Amount of Dissolved Oxygen Amount 1

The amount of the dissolved oxygen in the oxygen water produced in Example 1 was measured by conventional diaphragm method, Winkler method and fluorescence method, and by the method for measuring an amount of dissolved oxygen of the present invention (hereinafter the method for measuring an amount of dissolved oxygen of the present invention will be described as "carbohydrazide method" for the sake of convenience).

In the diaphragm method, a diaphragm type galvanic battery oxygen concentration meter (DO-31P manufactured by DKK-TOA Corporation) was used, and in the fluorescence method, a fluorescent dissolved oxygen meter (ProODO manufactured by YSI) was used.

In the carbohydrazide method, carbohydrazide (0.1 g) was added as a deoxygenating amino compound to the oxygen water (500 ml) produced in Example 1, and the dissolved oxygen and carbohydrazide in the oxygen water were reacted under heating at 80° C. for 4 hours. Thereafter the concentration of the carbohydrazide was measured by iodometry, and it was confirmed from the amount of the reacted carbohydrazide that the amount of the dissolved oxygen contained in the oxygen water was 55.0 ppm.

Furthermore, the dissolved oxygen and carbohydrazide in the oxygen water were reacted under heating conditions of 100° C. and 1 hour. Thereafter the concentration of the carbohydrazide was measured by iodometry in a similar manner, and it was confirmed from the amount of the reacted carbohydrazide that the amount of the dissolved oxygen contained in the oxygen water was 55.4 ppm.

On the other hand, for the oxygen water produced in Example 1, the concentration was measured to be 27 ppm by the diaphragm method, 28 ppm by the Winkler method, and 28 ppm by the fluorescence method.

The above-mentioned results are summarized in Table 1.

TABLE 1

| Carbohydrazide method (80° C.) | Carbohydrazide method (100° C.) | Diaphragm method | Winkler method | Fluorescence method |
| --- | --- | --- | --- | --- |
| 55.0 ppm | 55.4 ppm | 27 ppm | 28 ppm | 28 ppm |

In the results of the measurements of the amount of the dissolved oxygen in the oxygen water produced in Example 1, it was confirmed that there was a significant difference such that a numerical value P1 of the amount of the dissolved oxygen measured by the carbohydrazide method and a numerical value P2 of the amount of the dissolved oxygen measured by the diaphragm electrode method, Winkler method or fluorescence method is P1>P2. Since the carbohydrazide method includes the steps of adding carbohydrazide and heating at a high temperature, the whole oxygen in the oxygen water can be taken out and measured. On the other hand, it was confirmed that the whole oxygen in the oxygen water cannot be measured depending on the state of dissolution of oxygen in the conventional diaphragm method, Winkler method and fluorescence method.

Therefore, it is considered that the oxygen molecules are stably dissolved in the state of a clathrate hydrate containing oxygen molecules surrounded by a lattice of water molecules in the oxygen water produced in Example 1. Furthermore, the difference (P1-P2) between the numerical value P1 of the amount of the dissolved oxygen measured by the carbohydrazide method and the numerical value P2 of the amount of the dissolved oxygen measured by either of the conventional diaphragm method and fluorescence method indicates that latent dissolved oxygen that has not been able to be measured by the conventional diaphragm method or fluorescence method is present in the oxygen water produced in Example 1. It was confirmed that dissolved oxygen that has not been able to be measured by conventional methods can also be surely measured by the carbohydrazide method.

Comparative Example 1

For commercially available oxygen waters A and B, the amount of the dissolved oxygen after opening was measured. "Dissolved oxygen: 150 ppm" was indicated for the commercially available oxygen water A, but the amount of the dissolved oxygen decreased to 30 ppm immediately after opening. Furthermore, "Dissolved oxygen: 120 ppm" was indicated for the commercially available oxygen water B, but the amount of the dissolved oxygen decreased to 35 ppm immediately after opening.

For these commercially available oxygen waters A and B, the amount of the dissolved oxygen was measured by the carbohydrazide method and the fluorescence method.

(1) In the carbohydrazide method, carbohydrazide (0.1 g) was added to commercially available oxygen water A (500 ml) immediately after opening, and the dissolved oxygen and the carbohydrazide in the oxygen water were reacted under heating at 80° C. for 4 hours. Thereafter the concentration of the carbohydrazide was measured by iodometry, and it was confirmed that the amount of the dissolved oxygen contained in the oxygen water A was 30 ppm from the amount of the reacted carbohydrazide. Furthermore, when the amount of the dissolved oxygen in the commercially available oxygen water A was measured by using a fluorescent dissolved oxygen meter (ProODO manufactured by YSI), it was confirmed that the amount of the dissolved oxygen contained in the oxygen water A was 30 ppm.

Specifically, it was confirmed that there was no difference between the numerical value P1 of the amount of the dissolved oxygen measured by the carbohydrazide method and the numerical value P2 of the amount of the dissolved oxygen measured by the fluorescence method in the oxygen water A, and thus the whole dissolved oxygen was able to be measured by the conventional method (oxygen dissolved in the form of a clathrate hydrate was absent).

(2) In the carbohydrazide method, carbohydrazide (0.1 g) was added to commercially available oxygen water B (500 ml) immediately after opening, and the dissolved oxygen and the carbohydrazide in the oxygen water were reacted under heating at 80° C. for 4 hours. Thereafter the concentration of the carbohydrazide was measured by iodometry, and it was confirmed that the amount of the dissolved oxygen contained in the oxygen water B was 35 ppm from the amount of the reacted carbohydrazide. Furthermore, when the amount of the dissolved oxygen in the commercially available oxygen water B was measured by using a fluorescent dissolved oxygen meter (ProODO manufactured by YSI), it was confirmed that the amount of the dissolved oxygen contained in the oxygen water B was 35 ppm.

Specifically, it was confirmed that there was no difference between the numerical value P1 of the amount of the dissolved oxygen measured by the carbohydrazide method and the numerical value P2 of the amount of the dissolved oxygen measured by the fluorescence method in the oxygen water B, and thus the whole dissolved oxygen was able to be measured by the conventional method (oxygen dissolved in the form of a clathrate hydrate was absent).

The invention claimed is:

1. A method for measuring an amount of dissolved oxygen contained in a liquid sample, comprising the steps of:
   (1) adding a deoxygenating amino compound to a liquid sample to prepare the liquid sample having a predetermined concentration of the deoxygenating amino compound;
   (2) after Step (1), heating the liquid sample containing the deoxygenating amino compound at a temperature of 80° C. or more for a predetermined time such that the dissolved oxygen fully reacts with the deoxygenating amino compound;
   (3) after Step (2), measuring the concentration of the deoxygenating amino compound contained in the liquid sample; and
   (4) calculating the amount of the dissolved oxygen contained in the liquid sample in Step (1) from the amount of the deoxygenating amino compound that reacted with the dissolved oxygen in Step (2) by comparing the concentration of the deoxygenating amino compound measured in Step (3) and the predetermined concentration of the deoxygenating amino compound in Step (1).

2. The method for measuring an amount of dissolved oxygen according to claim 1, wherein the deoxygenating amino compound is selected from the group consisting of carbohydrazide, diethylhydroxylamine, hydroxydiaminobenzene, isopropylhydroxylamine, and mixtures thereof.

3. The method for measuring an amount of dissolved oxygen according to claim 1, wherein the predetermined concentration of the deoxygenating amino compound in the liquid sample is 0.01 to 2% in Step (1).

4. The method for measuring an amount of dissolved oxygen according to claim 1, wherein the concentration of the deoxygenating amino compound in Step (3) is measured by iodometry.

* * * * *